United States Patent [19]

Duncan

[11] Patent Number: 4,872,219
[45] Date of Patent: * Oct. 10, 1989

[54] SELF-SUPPORTING EAR PROTECTOR

[76] Inventor: Karen Duncan, 15 Palmer St., Cos Cob, Conn. 06870

[*] Notice: The portion of the term of this patent subsequent to Dec. 22, 2004 has been disclaimed.

[21] Appl. No.: 189,384

[22] Filed: May 2, 1988

[51] Int. Cl.$^4$ .......................... A61F 11/00; A42B 1/06
[52] U.S. Cl. .......................................... 2/209; 128/866
[58] Field of Search ............................ 2/209, 174, 275; 128/866

[56] References Cited

U.S. PATENT DOCUMENTS

| | | | |
|---|---|---|---|
| 2,325,150 | 7/1943 | Sahlmann | 2/209 |
| 2,378,398 | 6/1945 | Feidler | 2/209 |
| 2,444,251 | 6/1948 | Goldman | 2/209 |
| 2,582,907 | 1/1952 | Kaufmann | 2/209 |
| 3,112,493 | 12/1963 | Greenberg | 2/209 |
| 4,713,843 | 12/1987 | Duncan | 2/209 |

Primary Examiner—Werner H. Schroeder
Assistant Examiner—Sara M. Current

[57] ABSTRACT

A self-supporting ear protector includes a unitary flexible core member formed from a flat, elongated rectangular sheet of a resilient, flexible plastic material substantially impervious to cold weather conditions, the sheet being molded and cut to form a ring shape of substantially constant thickness having a general configuration of the ear to be protected. The ring shape defines a first central opening therein; an outer protective exposed layer of material secured to one side of the sheet of plastic material in covering relation to the first central opening, the outer layer having an outer surface which can be imprinted and an inner layer secured to the opposite side of the sheet of plastic material and having a second central opening in substantial alignment with the first central opening.

7 Claims, 2 Drawing Sheets

SELF-SUPPORTING EAR PROTECTOR

BACKGROUND OF THE INVENTION

This invention relates to an improvement over my invention described in U.S. Pat. No. 4,713,843 which is incorporated herein by reference.

That patent discloses a self-supporting ear protector having a flexible core member formed into a continuous loop of substantially constant thickness having the general configuration of an ear to be protected, an outer protective exposed layer secured to one side of said core member in covering relation to the central opening in the flexible member and an inner layer secured to the opposite side of the sheet of plastic material.

The flexible member is described to be formed of opposite edges abutting each other so as to form a convex configuration.

The convex configuration was an aspect that distinguished the invention in that patent from the prior art because where the prior art taught forming a convex shape, it also taught overlapping the ends of the element forming said shape which resulted in a bulky and cumbersome flexible core member.

It has been discovered that a flexible core member can be formed exhibiting the same properties of substantially constant thickness and having resilient flexible characteristics without first forming the member with a separation between the free ends thereof, with the ends then drawn to be sealed in an abutting relationship to provide the convex form.

In particular, this invention provides for an ear protector having all the improvements of those set forth in my prior patent, but which also includes forming the flexible member of a single unitary pre-cut plastic flat piece which is then heated on a mold into the desired convex shape which is retained after the plastic piece is cooled. Additionally, the flexible core member may also be formed by feeding sheets of polypropylene into a thermoforming apparatus. The sheets are heated over molds in the shape of the flexible core member having the general configuration of the ear. After the polypropylene sheet which carries the molded sections cools, the individual flexible core members are die cut. With either method, the resulting flexible member is resilient, flexible, can be snapped to fixed open and closed positions and has a substantially constant thickness.

This present core member is simpler to form, easily may be made of different plastic materials and can have its molded shape better controlled to more effectively serve to permit the ear protector to be removed and/or firmly held on the ear.

DETAILED DESCRIPTION OF A PREFERRED EMBODIMENT

Figure 1:
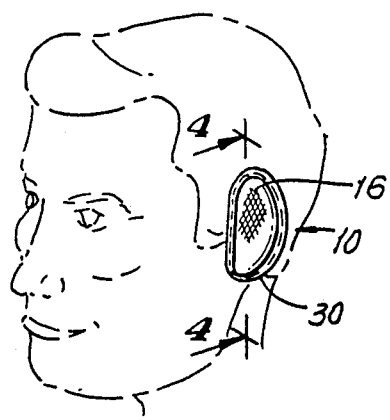
FIG. 1 is a perspective view of the ear protector according to the present invention, being worn.
Figure 2:
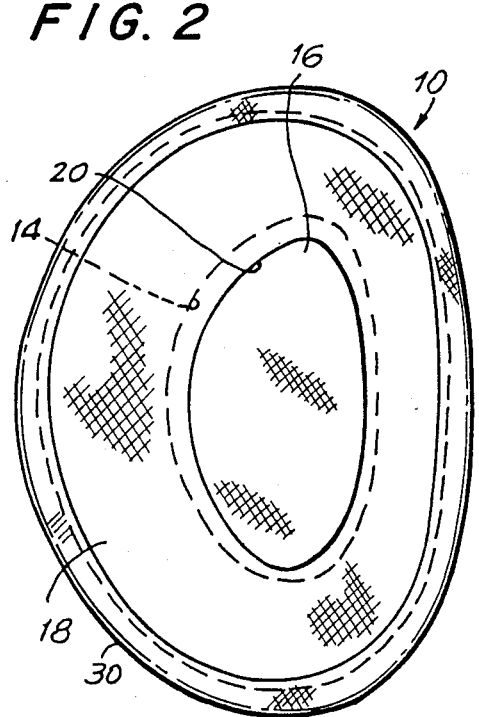
FIG. 2 is an inside elevational view of the ear protector of FIG. 1.
Figure 3:
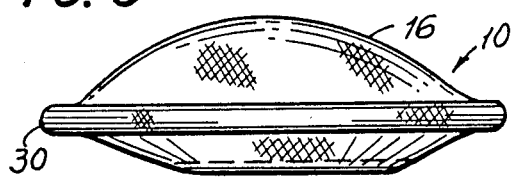
FIG. 3 is a top plan view of the ear protector of FIG. 1.

Referring to the drawings in detail, a self-supporting ear protector 10 according to the present invention is generally formed with a flexible core member 12 formed in the general configuration of an ear to be protected and having a central oval-shaped opening 14 therein, an outer protective layer 16 secured to an outer surface of core member 12, and an inner layer 18 secured to the opposite surface of core member 12 and having a central oval-shaped opening 20 in substantial alignment with central opening 14.

Specifically, core member 12 is formed from a flat, elongated rectangular sheet of resilient, flexible plastic material which is substantially impervious to cold weather conditions. As an example, core member 12 can be formed from polypropylene, and preferably has a thickness of approximately 0.15 inches which is uniform throughout the sheet. The sheet of plastic material is initially configured as a continuous flat ring, and the core member is formed by the thermoforming process described below.

Polypropylene sheets are fed into thermoforming machines where the material is heated over molds in the shape of the flexible core member having a general configuration of the ear. Vacuum pressure is then applied to the polypropylene covering the molds and the shape of the molds is then recreated in the polypropylene. The polypropylene is then cooled and released from the molds. It is then die cut around the outer edges of this thermoformed shape and also in the center, creating a hole large enough for the ear.

The core member 12 if formed into a generally convex shape according to the above process, and the polypropylene material is resilient so that it can snap to an open position allowing the ear protector to be removed from the ear and to a closed convex shape allowing the ear protector to hug the ear. It will be appreciated that because of the manner of formation of core member 12, core member 12 is formed in a slightly bent configuration, having a concave inner surface 26 and a convex outer surface 28, as best shown in FIG. 4 so as to better conform to the configuration of the ear to be protected.

Outer protective layer 16 is secured to the opposite inner surface 26 of core member 12 at the outer periphery thereof such that central opening 20 thereof is in substantial alignment with central opening 14 of core member 12.

Figure 4:
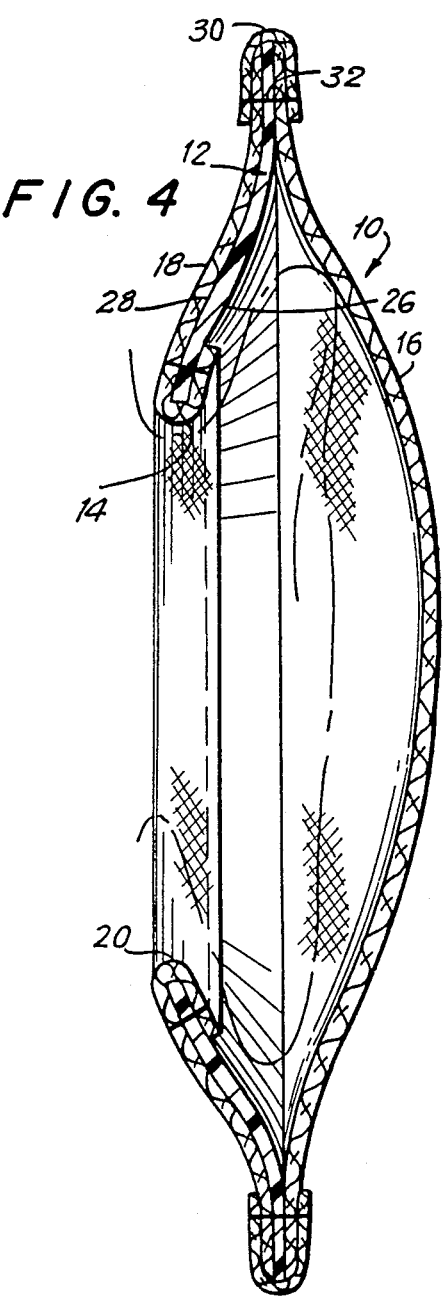
FIG. 4 is a cross-sectional view of the ear protector of FIG. 1, taken along line 4—4 thereof.
Figure 5:
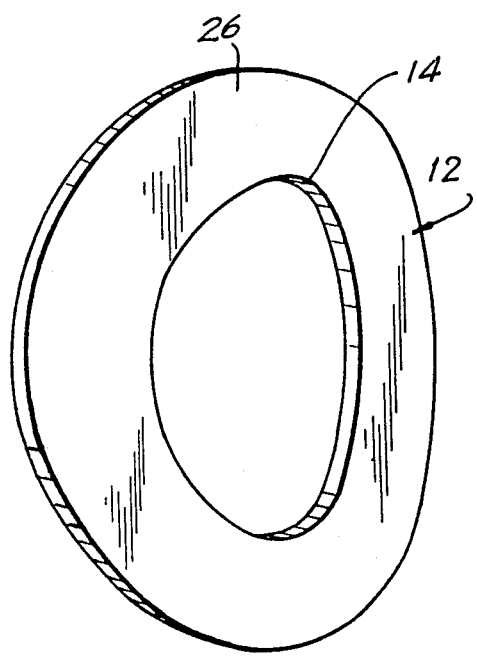
FIG. 5 is a perspective view of the flexible core member of the ear protector of FIG. 1.

To secure outer protective layer 16 and inner layer 18 to core member 12, a reinforcing material 30 is preferably wrapped about inner layer 18, core member 12 and outer protective layer 16 at the outer periphery of core member 12, and stitching 32 is used to secure reinforcing material 30, inner layer 18, core member 12 and outer protective layer 16 together, as shown in FIG. 4.

In operation, due to the flexibility of the ear cartilege, the ear can be inserted through openings 20 and 14, as shown in FIG. 4. Once the ear is inserted, ear protector 10 is bent to conform to the ear surface. Specifically, due to the flexibility of core member 12, core member 12 is flexed toward the ear, allowing the ear protector to hug the ear and be held thereon.

The present invention, by providing a one-piece continuous thickness member 12 renders use of ear protector 10 comfortable to the wearer. Thus, ear protector 10 can be worn in total comfort, giving the wearer warmth with the security that the ear protector will not dislodge or otherwise fail to protect the ear during periods of activity under cold weather conditions, such as skiing or sledding.

Having described a specific preferred embodiment of the invention with reference to the accompanying drawings, it will be appreciated that the present invention is not limited to that precise embodiment, and that various changes and modifications can be effected therein by one of ordinary skill in the art without departing from the spirit or scope of the invention as defined in the appended claims.

What is claimed is:

1. An ear protector comprising:
   a flexible core member having a ring shape and formed of a unitary resilient, flexible plastic material substantially impervious to cold weather conditions and having substantially constant thickness, said core having a general configuration of an ear to be protected, said continuous loop defining a first central opening therein;
   an outer protective exposed layer of material secured to one side of said sheet of plastic material in covering relation to said first central opening; and
   an inner layer secured to an opposite side of said sheet of plastic material and having a second central opening in substantial alighment with said first central opening.

2. An ear protector according to claim 1; wherein said unitary core member comprises a molded polypropylene material.

3. An ear protector according to claim 1; wherein said core member is resiliently flexible and snaps to open and closed positions.

4. A protector according to claim 1; wherein said unitary core plastic material is vacuum molded.

5. A protector according to claim 4; wherein said unitary core is die cut from a plastic material to its ring shape.

6. An ear protector according to claim 1; wherein said core member has a substantially constant thickness of 0.15 inches.

7. An ear protector according to claim 1; wherein said core member has an outer convex surface and an inner concave surface.

* * * * *